United States Patent [19]

Owen et al.

[11] Patent Number: 4,628,135
[45] Date of Patent: Dec. 9, 1986

[54] INTEGRATED PROCESS FOR CONVERTING OXYGENATES TO LIQUID HYDROCARBONS

[75] Inventors: Hartley Owen, Belle Mead; Samuel A. Tabak, Wenonah; Bernard S. Wright, East Windsor, all of N.J.

[73] Assignee: Mobil Oil Corporation, New York, N.Y.

[21] Appl. No.: 779,363

[22] Filed: Sep. 23, 1985

[51] Int. Cl.$^4$ .................... C07C 1/20; C07C 2/00
[52] U.S. Cl. ................................ 585/331; 585/315; 585/316; 585/640; 585/709; 585/723
[58] Field of Search ............... 585/331, 315, 316, 640, 585/709, 7 SM, 723

[56] References Cited

U.S. PATENT DOCUMENTS

| | | | |
|---|---|---|---|
| 3,972,958 | 8/1976 | Garwood et al. | 585/469 |
| 4,048,250 | 9/1977 | Garwood et al. | 585/659 |
| 4,211,885 | 7/1980 | Banks | 585/415 |
| 4,262,155 | 4/1981 | Hutson, Jr. | 585/331 |
| 4,423,274 | 12/1983 | Daviduk et al. | 585/640 |
| 4,433,185 | 2/1984 | Tabak | 585/312 |
| 4,482,772 | 11/1984 | Tabak | 585/254 |
| 4,506,106 | 3/1985 | Hsia et al. | 585/312 |
| 4,543,435 | 9/1985 | Gould et al. | 585/330 |
| 4,547,602 | 10/1985 | Tabak | 585/314 |

*Primary Examiner*—Asok Pal
*Attorney, Agent, or Firm*—A. J. McKillop; M. G. Gilman; L. G. Wise

[57] ABSTRACT

Alkylate is produced by catalytically converting oxygenate feedstock, such as methanol, to lower olefins comprising dominantly $C_2$–$C_4$ olefins. Ethene is separated from primary stage effluent by interstage sorption of $C_3+$ components which may be upgraded. Isoparaffin may be alkylated with $C_3$–$C_4$ olefins in a secondary stage.

The improved technique comprises fractionating an olefinic feedstream containing ethene and $C_3+$ olefinic components by contacting the olefinic feedstream in a sorption zone with a liquid hydrocarbon sorbent to selectively sorb $C_3+$ components;
wherein the sorbent is obtained by condensing $C_5+$ aliphatic and aromatic hydrocarbon from the primary stage.

12 Claims, 2 Drawing Figures

INTEGRATED PROCESS FOR CONVERTING OXYGENATES TO LIQUID HYDROCARBONS

BACKGROUND OF THE INVENTION

This invention relates to an integrated system for converting oxygenates, such as methanol or dimethyl ether (DME), to liquid hydrocarbons. In particular it provides a continuous process for producing liquid hydrocarbon products by converting the oxygenate feedstock catalytically to an intermediate lower olefinic stream for upgrading to produce light distillate and/or gasoline products.

In order to provide an adequate supply of liquid hydrocarbons for use as synfuels or chemical feedstocks, various processes have been developed for converting coal and natural gas to gasoline and distillate. A substantial body of technology has grown to provide oxygenated intermediates, especially methanol. Large scale plants can convert methanol or similar aliphatic oxygenates to liquid fuels, especially gasoline. However, the demand for heavier hydrocarbons has led to the development of processes for making high octane gasoline and quality diesel fuel by a multi-stage technique, utilizing mainly $C_3+$ olefins for upgrading.

Recent developments in zeolite catalysts and hydrocarbon conversion processes have created interest in utilizing olefinic feedstocks for producing $C_5+$ gasoline, diesel fuel, etc. In addition to the basic work derived from ZSM-5 type zeolite catalysts, a number of discoveries have contributed to the development of new industrial processes.

The medium pore ZSM-5 type catalysts are particularly useful for converting methanol and other lower aliphatic alcohols or corresponding ethers to olefins. Particular interest has been directed to a catalytic process for converting low cost methanol to valuable hydrocarbons rich in ethene and $C_3+$ alkenes. Various processes are described in U.S. Pat. Nos. 3,894,107 (Butter et al), 3,928,483 (Chang et al), 4,025,571 (Lago), 4,423,274 (Daviduk et al) and 4,433,189 (Young), incorporated herein by reference. It is generally known that the methanol-to-olefins (MTO) process can be optimized to produce a major fraction of $C_2-C_4$ olefins. Prior process proposals have included a separation section to recover ethene and other gases from byproduct water and $C_5+$ hydrocarbon liquids.

SUMMARY OF THE INVENTION

It has been discovered that methanol, DME or the like may be converted to liquid fuels, particularly alkylate, in a multi-stage continuous process, with integration between the major process units providing an ethene-rich recycle stream for further conversion and liquid recycle stream for interstage sorption utilizing $C_5+$ liquid from the MTO stage as sorbent. $C_3+$ olefins from the initial stage MTO type process hydrocarbon effluent stream, after byproduct hydrocarbon and water separation, can be fed to an alkylation stage for upgrading to heavier hydrocarbons. Ethene may be recovered by interstage separation and recycled. Advantageously, the recycled ethene is found to be reactive with methanol/DME or other oxygenates in the presence of ZSM-5 type catalysts. In effect a novel MTO and olefin upgrading system is provided wherein the ethene component may be recycled substantially to extinction.

In a preferred embodiment, the invention provides processes and apparatus for an integrated continuous technique for converting oxygenated organic feedstock to liquid alkylate hydrocarbons comprising methods and means for (a) contacting feedstock with zeolite catalyst in a primary catalyst stage at elevated temperature to convert at least a portion of the feedstock oxygenate predominantly to an olefinic fraction rich in $C_2-C_4$ olefins and a minor heavy hydrocarbon portion containing $C_5+$ aliphatic and aromatic hydrocarbons;

(b) cooling and separating effluent from step (a) to provide an aqueous liquid byproduct stream, a heavy hydrocarbon liquid stream and a light hydrocarbon stream rich in $C_2-C_4$ olefins;

(c) compressing and contacting the light hydrocarbon stream in a sorption tower with a liquid hydrocarbon sorbent stream containing a major amount of said heavy liquid stream from step (b) to selectively sorb $C_3+$ components in a liquid sorbate stream;

(d) fractionating the sorbate stream to provide a gasoline-rich stream and a light hydrocarbon stream rich in $C_3-C_4$ olefins;

(e) further reacting the olefinic light hydrocarbon stream from step (d) with isoparaffin in a secondary alkylation stage in the presence of liquid phase acid catalyst to convert at least a portion of $C_3-C_4$ olefins to a heavier $C_7+$ liquid hydrocarbon product stream comprising alkylate gasoline;

(f) recycling ethene in a gaseous stream from the sorption tower to the primary catalytic stage for further converion; and (g) recycling a portion of gasoline from step (d) to step (c) for use as lean sorbent.

Advantageously, the primary stage catalyst comprises ZSM-5 type zeolite and ethene is recycled to the primary stage at a rate of about 1 to 20 parts ethene per 100 parts by weight of methanol equivalent in the feedstock. By fractionating gaseous effluent separated from the primary staged effluent, a recycle gas stream may be recovered containing at least 90% of ethene from the primary catalytic stage. An olefinic stream rich in $C_3+$ olefins, especially propene and butylenes, is provided for upgrading by reaction with various isoparaffins, such as isobutane.

Other objects and features of the invention will be seen in the following description and drawings.

THE DRAWINGS

FIG. 1 is a process flow sheet showing the major unit operations and process streams; and FIG. 2 is a schematic representation of an alternative inter-stage separation system.

DESCRIPTION OF PREFERRED EMBODIMENTS

Figure 1:
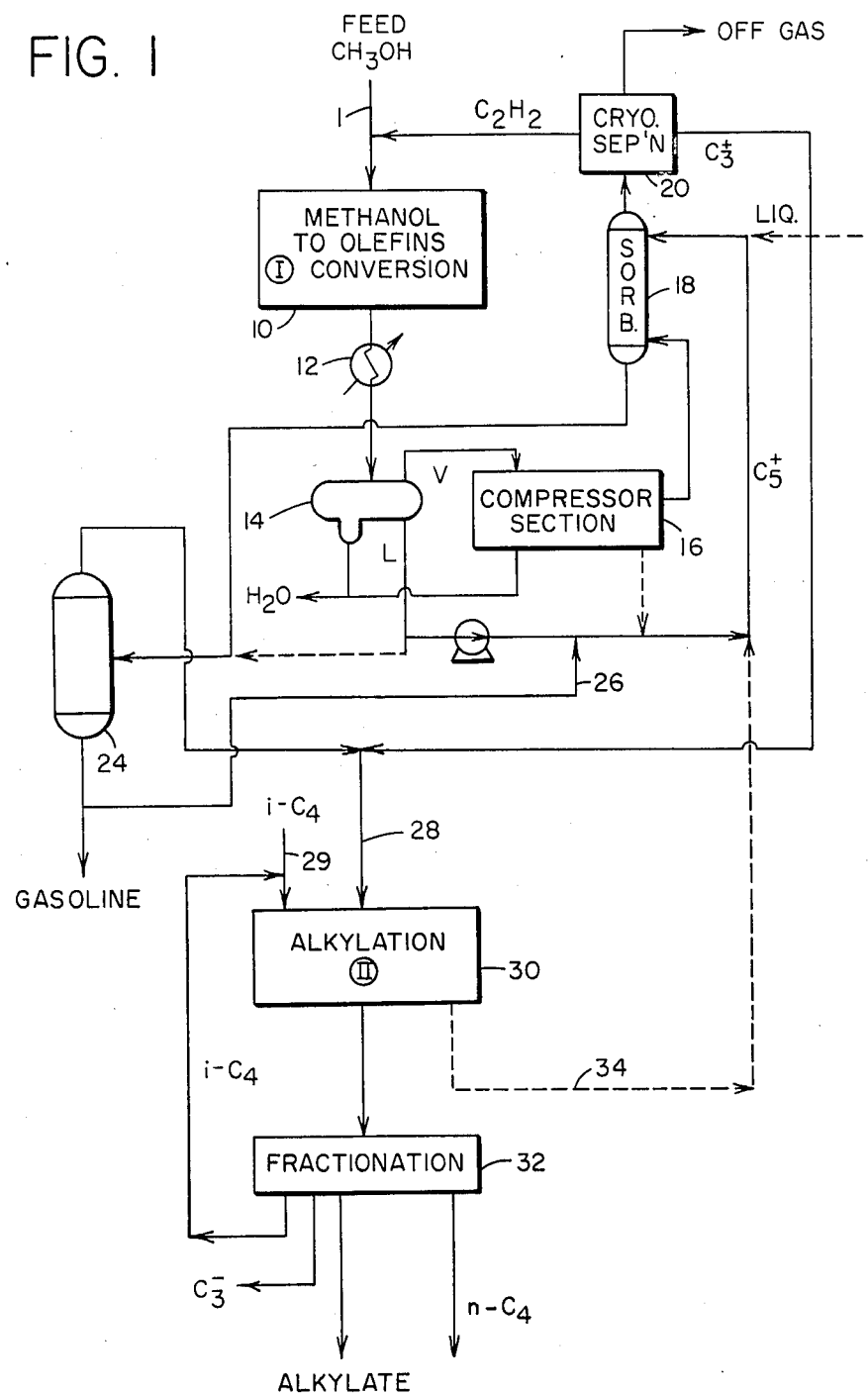

Numerous oxygenated organic compounds may be contained in the feedstock material to be converted in the primary stage. Since methanol or its ether derivative (DME) are industrial commodities available from synthesis gas or the like, these materials are utilized in the description herein as preferred starting materials. It is understood by those skilled in the art that MTO-type processes can employ methanol, dimethylether and mixtures thereof, as well as other aliphatic alcohols, ethers, ketones, and/or aldehydes. It is known in the art to partially convert oxygenates by dehydration, as in the catalytic reaction of methanol over gamma-alumina to produce DME intermediate. Typically, an equilibrium mixture ($CH_3OH+CH_3OCH_3+H_2$) is produced by partial dehydration. This reaction takes place in either conversion of methanol to lower olefins (MTO) or methanol to gasoline (MTG).

The process may be optimized by employing fluid bed primary stage conditions in the temperature range of about 425° C. to 550° C., a pressure range of about 100 to 800 kPa and weight hourly space velocity range of about 0.5 to 3.0 based on ZSM-5 equivalent catalyst and methanol equivalent in the primary stage feedstock. Suitable equipment and operating conditions are described in U.S. patent application Ser. No. 687,405 filed Dec. 28, 1984, incorporated herein by reference.

The zeolite catalysts preferred for use herein include the crystalline aluminosilicate zeolites having a silica to alumina ratio of at least 12, a constraint index of about 1 to 12 and acid cracking activity of about 1–200. Representative of the ZSM-5 type zeolites are ZSM-5, ZSM-11, ZSM-12, ZSM-22, ZSM-23, ZSM-35 and ZSM-38. ZSM-5 is disclosed and claims in U.S. Pat. No. 3,702,886 and U.S. Pat. No. Re. 29,948; ZSM-11 is disclosed and claimed in U.S. Pat. 3,709,979. Also, see U.S. Pat. No. 3,832,449 for ZSM-12; U.S. Pat. No. 4,076,979. Also, see U.S. Pat. No. 3,832,449 for ZSM-12; U.S. Pat. No. 4,076,842 for ZSM-23; U.S. Pat. No. 4,016,245 for ZSM-35 and U.S. Pat. No. 4,046,839 for ZSM-38. The disclosures of these patents are incorporated herein by reference. A suitable catalyst for oxygenate conversion is HZSM-5 zeolite with alumina binder. These medium pore shape selective catalysts are sometimes known as porontectosilicates or "pentasil" catalysts.

Other catalysts and processes suitable for converting methanol/DME to lower olefins are disclosed in U.S. Pat. No. 4,493,263 (Vogt et al.) and European Patent Application 0081683 (Marosi et al.), and ZSM-45. In addition to the preferred aluminosilicates, the borosilicate, ferrosilicate and "silicalite" materials may be employed. ZSM-5 type catalysts are particularly advantageous because the same material may be employed for dehydration of methanol to DME, conversion to lower olefins and ethylene conversion.

In this description, metric units and parts by weight are employed unless otherwise stated. Various reactor configurations may be used, including fluidized bed catalytic reactors, moving bed and fixed bed reactors.

Referring to FIG. 1, the process feedstock (methanol or DME, for instance) is fed via conduit 1 to the primary MTO stage 10 where it is converted to lower olefins and $C_5+$ gasoline hydrocarbon plus water by dehydration of the oxygenated feedstock. The primary effluent is cooled by exchanger 12 and byproduct water is recovered by phase separation unit 14 from the cooled effluent. Liquid hydrocarbons L consisting essentially of $C_5+$ gasoline range materials are recovered from unit 14 and pumped to the absorber unit 18 at higher (secondary stage) pressure. Optionally, the heavy liquid condensed from MTO liquid may be sent to a fractionation system, as indicated by dashed line, to recover aromatics rich $C_6+$ components. Alternatively, MTO heavy liquid can be prefractionated to recover $C_9+$ aromatics as a separate stream.

Vapor phase effluent V from the primary stage may be compressed to alkylation reaction pressure in unit 16. Propylene, butylenes and amylenes may be separated from the primary stage effluent by sorption fractionation unit 18 to recover a recycle gas stream containing ethene from the primary stage and an olefinic sorbate stream rich in $C_3+$ olefins. Purified ethene (ie—90+%) can be obtained from cryogenic separation unit 21. A $C_3-C_4$ rich olefinic stream may be further prepared for reaction with isobutane or the like at high pressure and low temperature in contact with liquid phase acidic alkylation catalyst. The $C_3+0$ sorbate stream from sorber unit 18 is fractionated in tower 24 to recover $C_6+$ aromatic and aliphatic components. A portion of the gasoline tower bottom is recycled to the sorber 18 as lean sorbent via line 26. Thus the lower olefins and other $C_2-C_5$ aliphatic component are fed via conduit 28 for upgrading by reaction in the alkylation stage 30. Fresh isoparaffin (e.g.–i-$C_4$) and recycle are fed via conduit 29. Secondary stage alkylation effluent is then separated into $C_3-$ light gases, isobutane recycle, n-$C_4$ aliphatics and $C_5+$ gasoline and/or light distillate range alkylate hydrocarbons. Advantageously, isobutane is separated from the second stage effluent for recycle to provide a stoichiometric excess and added with fresh feed (i-$C_4$) to the unit. Optionally, as indicated by dashed line 34, a portion of the liquid paraffin-rich hydrocarbon may be recycled to the interstage sorption unit 18 to supplement the MTO liquids as lean sorbent. The preferred sorption unit is a countercurrent packed tower. Advantageously, the sorbent liquid comprises at least 50–75 wt% of $C_6+$ hydrocarbons which are the primary stage MTO reaction product. This lean sorbent has excellent properties for selective sorption of the propene, butylene and $C_3+$ paraffinic components of the primary stage light hydrocarbons. Unfractionated liquid alkylation effluent may be recycled in part, as depicted by dashed line.

Figure 2:
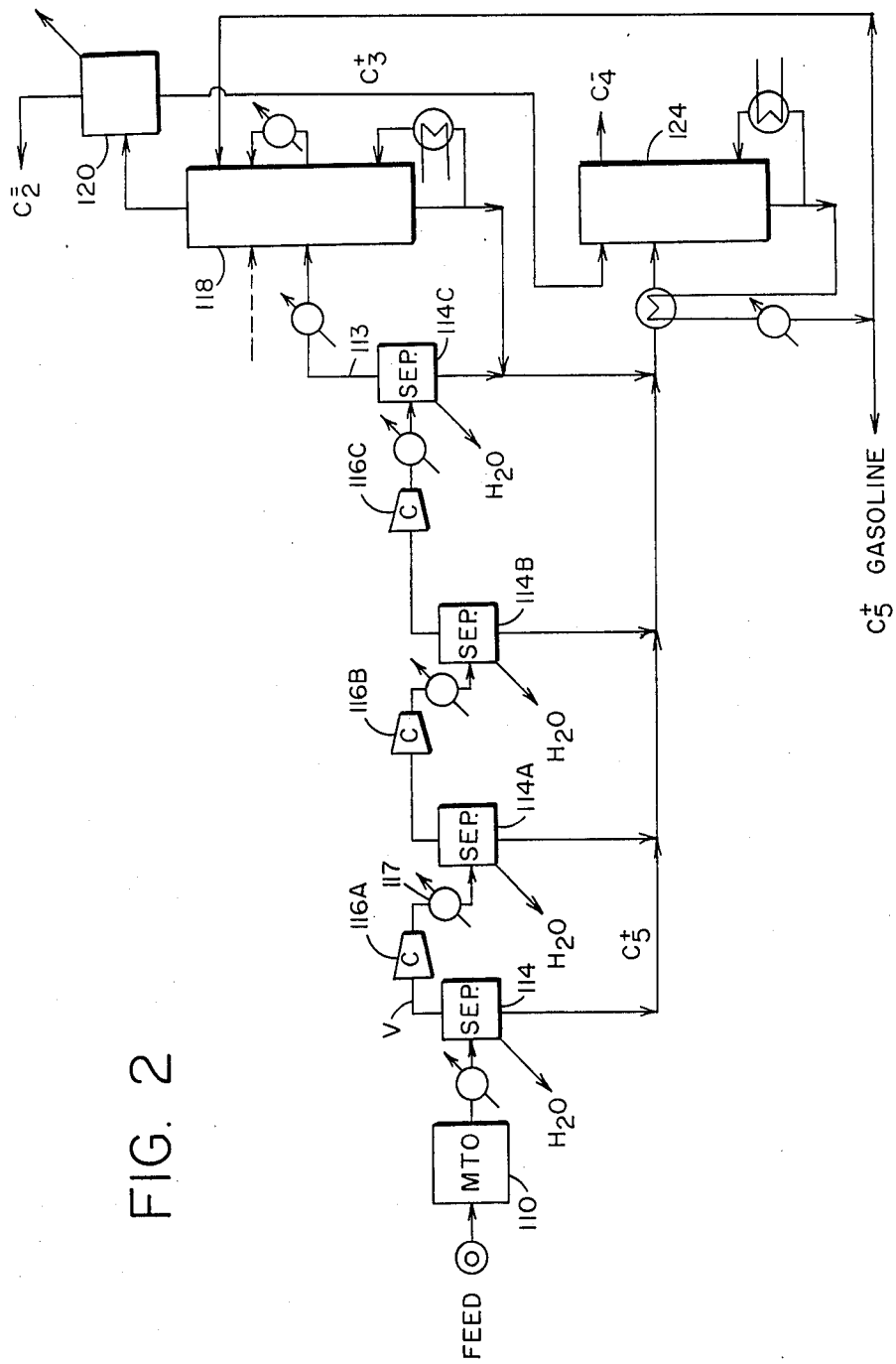

In the embodiment of FIG. 2, oxygenate feedstock is converted in MTO unit 110, cooled and passed to separator 114 to provide a $C_5+$ liquid stream. The light hydrocarbon vapor stream V separated from the primary stage effluent is compressed in a plurality of compression stages to condense liquid olefinic hydrocarbons. The liquid stream is combined with a condensed liquid from succeeding separators. The primary vapor stream is adiabatically compressed by compressor 116A, cooled by exchanger 117 and passed to a succeeding separator 114A, at which point the preceeding phase separation technique is repeated. Likewise other compressor 116B, C separators 114B and 114C operate to provide an ethene-rich recycle stream which is passed via line 113 to sorption fractionation unit 118 and optional cryogenic unit 120. Advantageously, the MTO effluent is received at about atmospheric pressure (eg, 100–150 kPa) and compressed in plural stages to a pressure of about 1500–3000 kPa and separated in the final vessel 114C at about ambient temperature (20°–80° C.). Olefinic liquids rich in $C_3+$ aliphatics may be recovered from the final compressor stage and passed with $C_5+$ liquid hydrocarbon stream to fractionation tower 124 where $C_5+$ gasoline recycle and product are recovered.

A suitable selective sorption unit is disclosed in U.S. Pat. No. 4,497,968 (Hsia et al), incorporated herein by reference. Ethene-rich vapor withdrawn from the separator 114C can be processed to increase ethene purity to at least 50% in sorption unit 118. This can be achieved by selectively absorbing $C_3+$ components in a $C_5+$ liquid hydrocarbon sorbent stream comprising aliphatic and aromatic hydrocarbons generated in the MTO unit.

The data in Table I represents a material balance and absorber operating conditions for a countercurrent contact tower unit design according to FIG. 2 and Runs 1–3. The vertical tower has 19 theoretical stages, with C6+ gasoline lean oil from the interstage sorbate fractionator being introduced at the top (stage 1), olefin vapor and liquid feed being fed at stages 9 and 10 respectively. Heat of sorption is removed by pumparound cooling at stages 5 and 8. The three runs correspond to 5 different lean oil rates. In the overhead stream, molar units are gm-moles per metric tonne (MT) of methanol charged to the process. The operating conditions are chosen to provide a maximum ethene content of 0.2 mol% in the sorbate.

Runs 4 to 6 (Table II) differ from runs 1 to 3 in that two lean oil compositions are employed. To the top stage is fed gasoline sorbent from the sorbate fractionator and to a lower stage (5) is fed heavy liquid separated from the MTO effluent, according to FIG. 1. Run 7 (Table III) is similar to run 4 except for sorbent rate and 1.5% ethene in the sorbate. Run 8 is similar to run 1 except for 0.1% ethene in the sorbate. Run 9 is similar to run 7 except for the use of compression section recontact between condensate and vapor prior to the sorption unit.

TABLE 1

| Run No. | 1 | 2 | 3 |
|---|---|---|---|
| Lean Oil* Rate (Stage 1) moles/ton MeOH charge | 5.45 | 2.00 | 1.50 |
| Material Balance wt % of MeOH charge | | | |
| (1) $C_6$ + MTO Gasoline (net) | 11.5 | 11.5 | 11.5 |
| (2) Alkylate product | 58.2 | 58.1 | 58.0 |
| (3) n-butane product | 0.6 | 0.6 | 0.6 |
| (4) propane product | 3.9 | 3.9 | 3.9 |
| (5) offgas | 1.5 | 1.6 | 1.6 |
| (6) water byproduct | 56.4 | 56.4 | 56.4 |
| (7) i-$C_4$ makeup | −32.1 | −32.1 | −32.0 |
| (8) methanol charge | −100.0 | −100.0 | −100.0 |
| Total | 5.45 | 2.00 | 1.50 |
| Overhead flow, SCM/ton MeOH | 41.0 | 44.0 | 47.6 |
| propane, moles/1000 tons MeOH | 0.0 | 5.8 | 15.9 |
| propylene | 0.8 | 111.8 | 250.0 |
| n-butane | 0.0 | 0.0 | 0.0 |
| isobutane | 0.0 | 0.0 | 0.0 |
| 1-butylene | 0.0 | 0.0 | 0.0 |
| n-pentanes | 0.2 | 0.2 | 0.3 |
| iso-pentanes | 0.4 | 0.4 | 0.4 |
| pentanes | 1.7 | 2.0 | 2.0 |
| $C_6$+ | 22.4 | 22.9 | 23.7 |
| Overhead pressure, kPa | 2068 | 2068 | 2068 |
| Cooling pump around, MJ/ton MeOH | −22.0 | −24.6 | −21.3 |
| Absorber Reboiler Duty MJ/ton MeOH | 211.4 | 117.7 | 107.1 |
| Ethene recovery in Overhead g-moles/tonne MeOH | 937 | 937 | 937 |
| Mole % | 54% | 50% | 47% |

*MTO Gasoline

TABLE II

| Run No. | 4 | 5 | 6 |
|---|---|---|---|
| Material Balance wt % of MeOH charge | | | |
| (1) $C_6$+ MTO gasoline | 11.4 | 11.4 | 11.4 |
| (2) Alkylate | 58.3 | 58.2 | 58.2 |
| (3) n-butane | 0.6 | 0.6 | 0.6 |
| (4) propane | 3.8 | 3.9 | 3.8 |
| (5) offgas | 1.6 | 1.6 | 1.7 |
| (6) water | 56.4 | 56.4 | 56.4 |
| (7) i$C_4$ | −32.1 | −32.1 | −32.1 |
| (8) methanol | −100.0 | −100.0 | −100.0 |
| Absorber Efficiency* | | | |
| Lean Oil 1 (stage 1) moles/ton MeOH | 4.44 | 1.39 | 0.74 |
| Lean Oil 2 (stage 5) | 1.01 | 1.01 | 1.01 |
| Total | 5.45 | 2.40 | 1.70 |
| Overhead flow, SCM/ton MeOH | 41.1 | 44.1 | 49.0 |
| propene, g-moles/tonne MeOH | 0.1 | 6.3 | 20.4 |
| propylene | 1.3 | 109.0 | 292.5 |
| n-butane | 0. | 0. | 0.2 |
| isobutane | 0. | 0.2 | 1.6 |
| i-butylene | 0. | 0.8 | 6.4 |
| n-pentanes | 0.2 | 0.2 | 0.3 |
| iso-pentanes | 0.4 | 0.4 | 0.5 |
| pentanes | 1.7 | 1.9 | 2.0 |
| $C_6$+ | 15.8 | 22.9 | 23.7 |
| Overhead pressure, kPa | 2068 | 2068 | 2068 |
| Cooling Pump around, MJ/ton MeOH | −29.1 | −33.2 | −30.1 |
| Reboiler Duty, MJ/ton MeOH | 181.0 | 104.8 | 91.9 |
| Ethylene recovery in Overhead g-moles/tonne MeOH | 938 | 938 | 938 |
| Mole % purity | 54 | 50 | 45 |

*based on 0.2 mol % $C_2$ in bottoms
Lean oil 1 - MTO Gasoline
Lean oil 2 - Heavy Liquid

TABLE III

| Run No. Absorber Efficiency | 7<br>1.5% $C_2$ in bottoms | 8<br>0.1% $C_2$ in bottoms | 9<br>1.5% $C_2$ in bottoms |
|---|---|---|---|
| Lean Oil #1* moles/ton MeOH | 1.00 | 4.00 | 1.00 |
| Lean Oil #2** moles/ton MeOH | 3.00 | | 3.00 |
| Total | 4.00 | 4.00 | 4.00 |
| Overhead flow, SCM/ton/MeOH | 40.0 | 40.3 | 36.2 |
| propene, g-moles/tonne MeOH | 13.0 | 2.1 | 9.9 |
| propylene | 144.4 | 48.7 | 106.6 |
| n-butane | 1.4 | 0.5 | 1.3 |
| isobutane | 5.1 | 0.3 | 4.5 |
| 1-butylene | 28.6 | 3.6 | 26.1 |
| n-pentanes | 0.8 | 1.6 | 0.7 |
| iso-pentanes | 21.4 | 47.5 | 19.9 |
| pentanes | 21.4 | 47.5 | 19.9 |
| $C_6$+ | 9.5 | 13.2 | 8.7 |
| Overhead pressure, kPa | 2068 | 2068 | 2068 |
| Cooling Pump around MJ/tonne MeOH | −3.2 | −36.0 | −3.1 |
| Reboiler Duty, MJ/tonne MeOH | 75.0 | 126.3 | 73.3 |
| Ethylene recovery in Overhead g-moles/tonne MeOH | 761 | 848 | 686 |
| Mole % purity | 45 | 50 | 45 |

*MTO gasoline  ⎫ both fed on stage 1
**MTO Heavy Olefin liquid  ⎭

The alkylation process employed herein for upgrading olefins is a well known industrial technique for reacting alkenes with tertiary alkanes (isoparaffins), such as isobutane, isopentane, isohexane, etc. The resulting product is a $C_7$+ branched chain paraffinic material useful as aviation gasoline, jet fuel or the like. The alkylation of paraffins can be carried out either thermally or catalytically; however, acid catalyst is preferred. Thermal or noncatalytic alkylation of a paraffin with an olefin is carried out at high temperatures (about 500° C.) and pressures 21–41 MPa (3000–6000 psi). Under these conditions, both normal and isoparaffins can be brought into reaction by a free-radical mechanism. Thermal alkylation is not known to be practiced commercially.

The catalytic alkylation of paraffins involves the addition of an isoparaffin containing a tertiary hydrogen to an olefin. The process is used in the petroleum industry to prepare highly branched paraffins mainly in the $C_7$ to $C_9$ range, that are high-quality fuels. The overall process is complex, requiring control of operating conditions and of catalyst. The process conditions and the product composition depend on the particular hydrocarbons involved.

The preferred processes are those brought about by the conventional protonic and Lewis catalysts. Propene can be brought into reaction with an isoparaffin in the presence of either concentrated sulfuric acid or hydrogen fluoride. The heptanes produced by alkylation of isobutane with propene are mainly 2,3- and 2,4-dimethylpentane. Propene is alkylated preferrably as a component of a $C_3$–$C_4$ fraction. HF catalysts for alkylation of isobutane with 1- and 2-butenes give both dimethylhexanes and trimethylpentanes. The product obtained from alkylation of isobutane with isobutylene at low temperature (e.g., −25° C.) with hydrogen fluoride is 2,2,4-trimethylpentane.

During use the acid catalysts may become diluted with byproduct hydrocarbons and as a result decrease in activity. Sulfuric acid concentrations are maintained at about 90%. Hydrogen fluoride concentrations of 80–90% are common, although the optimum concentration depends on the reaction temperature and reactor geometry. Operation below these acid concentrations generally causes incomplete conversion or polymerization. With sulfuric acid, the product quality is improved when temperatures are reduced to the range of 0°–10° C. Cooling requirements are obtained by low temperature flashing of unreacted isobutane. With hydrogen fluoride, the reaction process is less sensitive to temperature, and temperatures of 0°–40° C. can be used. Some form of heat removal is essential because the heat of reaction is approximately $14 \times 10^5$ J/kg (600 Btu/lb) of butenes converted. Typically the elevated pressure for alkylation by these acid catalysts is about 1500 to 3000 kPa (200–300 psig).

In order to prevent polymerization of the olefin as charged, an excess of isobutane is present in the reaction zone. Isobutane-to-olefin molar ratios of 6:1 to 14:1 are common, more effective suppression of side reactions being produced by the higher ratios.

The typical alkylation reaction employs a two-phase system with a low solubility of the isobutane in the catalyst phase. In order to ensure intimate contact of reactants and catalyst, efficient mixing is provided. This is important with sulfuric acid because of the low solubility of isobutane in the catalyst phase. In addition, the higher viscosity of the sulfuric acid requires a greater mixing energy to assure good contact. The solubility of the hydrocarbon reactants in the catalyst phase is increased by the presence of the unsaturated organic diluent held by the acid catalyst. This organic diluent also has been considered a source of carbonium ions that promote the alkylation reaction.

For the hydrofluoric acid system, reactive i-$C_4H_8$ readily alkylates to give an excellent product. The alkylation of pure 1-$C_4H_8$ by itself proceeds with considerable isomerization of the 1-$C_4H_8$ to 2-$C_4H_8$ followed by alkylation to give a highly branched product. The presence of i-$C_4H_8$ accelerates the alkylation reaction and allows less time for olefin isomerization. Consequently the reaction produces an alkylate with a lowered antiknock value. For the sulfuric acid system, i-$C_4H_8$ tends to oligomerize and causes other side reaction products of inferior quality; but the isomerization of 1-$C_4H_8$ to 2-$C_4H_8$ proceeds more completely, thereby favoring formation of superior products. Thus for mixed olefin feeds such as described above, the two factors with both catalyst systems counteract each other to provide products of similar antiknock properties.

The olefin-producing MTO process may simultaneously generate isobutane, but the amount may be insufficient to alkylate the coproduced olefins. A suitable outside source of isobutane is natural gas or a byproduct of methanol-to-gasoline (MTG) processes.

Suitable alkylation processes are described in U.S. Pat. Nos. 3,879,489 (Yurchak et al), 4,115,471 (Kesler), 4,377,721 (Chester) and in the Kirk-Othmer Encyclopedia of Chemical Technology, Vol. 2, pp. 50–58 (3rd Ed., 1978) John Wiley & Sons, incorporated herein by reference.

The combined processes are an effective means for converting oxygenated organic compounds, such as methanol, DME, lower aliphatic ketones, aldehydes, esters, etc, to valuable hydrocarbon products. Thermal integration is achieved by employing heat exchangers between various process streams, towers, absorbers, etc.

Various modifications can be made to the system, especially in the choice of equipment and non-critical processing steps. While the invention has been described by specific examples, there is no intent to limit the inventive concept as set forth in the following claims.

We claim:

1. An integrated continuous process for converting oxygenated organic feedstock to liquid hydrocarbons comprising the steps of
   (a) contacting feedstock with zeolite catalyst in a primary catalyst stage at elevated temperature to convert at least a portion of the feedstock oxygenate predominantly to an olefinic fraction rich in $C_2$–$C_4$ olefins and a minor heavy hydrocarbon portion containing $C_5+$ aliphatic and aromatic hydrocarbons;
   (b) cooling and separating effluent from step (a) to provide an aqueous liquid byproduct stream, a heavy hydrocarbon liquid stream and a light hydrocarbon stream rich in $C_2$–$C_4$ olefins;
   (c) compressing and contacting the light hydrocarbon stream in a sorption tower with a liquid hydrocarbon sorbent stream containing a major amount of said heavy liquid stream from step (b) to selectively sorb $C_3+$ components in a liquid sorbate stream;
   (d) fractionating the sorbate stream to provide a gasoline-rich stream and a light hydrocarbon stream rich in $C_3$–$C_4$ olefins;
   (e) further reacting the olefinic light hydrocarbon stream from step (d) with isoparaffin in a secondary alkylation stage in the presence of liquid phase acid catalyst to convert at least a portion of $C_3$–$C_4$ olefins to a heavier $C_7+$ liquid hydrocarbon product stream comprising alkylate gasoline;

(f) recycling ethene in a gaseous stream from the sorption tower to the primary catalytic stage for further conversion; and (g) recycling a portion of gasoline from step (d) to step (c) for use as lean sorbent.

2. The process of claim 1 wherein said isoparaffin comprises isobutane.

3. The process of claim 1 wherein the primary stage catalyst comprises ZSM-5 type zeolite and ethene is recycled to the primary stage at a rate of about 1 to 20 parts ethene per 100 parts by weight of methanol equivalent in the feedstock.

4. The process of claim 1 wherein primary stage feedstock comprising methanol and/or dimethyl ether and recycled ethene are converted over HZSM-5 catalyst to provide a light olefinic hydrocarbon vapor stream comprising a major amount of $C_3$–$C_4$ olefins and a minor amount of ethene.

5. The process of claim 4 wherein olefin production is optimized by employing fluid bed primary stage conditions in the temperature range of about 425° C. to 550° C., a pressure range of about 100 to 800 kPa and weight hourly space velocity range of about 0.5 to 3.0 based on ZSM-5 equivalent catalyst and methanol equivalent in the primary stage feedstock.

6. The process of claim 4 wherein primary stage hydrocarbon effluent contains about 1 to 10 wt.% ethene and about 10 to 60 wt.% $C_3$–$C_4$ olefins.

7. The process of claim 1 wherein the alkylation stage effluent is fractionated to provide a hydrocarbon product comprising $C_7$ to $C_9$ isoparaffin.

8. The process of claim 1 wherein the secondary alkylation stage comprises a liquid phase reaction catalyzed by HF.

9. A continuous process for converting oxygenated aliphatic feedstock to olefins comprising contacting the feedstock with a zeolite conversion catalyst in a primary catalytic stage at elevated temperature and low pressure to produce ethene, $C_3$–$C_4$ olefins and heavier hydrocarbons comprising $C_5+$ aliphatic and aromatic hydrocarbons components;

cooling and separating the primary stage effluent to provide an olefinic $C_4^-$ vapor stream and a liquid heavier hydrocarbon stream;

compressing the olefinic $C_4^-$ vapor stream and contacting at least a portion of the liquid heavier hydrocarbon stream with the compressed stream in a countercurrent sorption fractionator under pressure and conditions to selectively sorb $C_3+$ olefins from the compressed stream, thereby providing an ethene-rich vapor stream;

further upgrading the sorbed $C_3+$ olefins in a second catalytic stage to produce liquid hydrocarbon product.

10. The process of claim 9 wherein the olefinic $C_4^-$ vapor stream is compressed in multiple compression steps, thereby condensing a portion of the $C_3$–$C_4$ olefins as a pressurized liquid stream, combining said $C_3$–$C_4$ olefinic liquid with the liquid sorbate stream comprising $C_3+$ olefins from the sorption fractionator;

further fractionating the combined liquid streams in debutanizing tower to provide a $C_4^-$ feedstream to the second catalytic stage and a $C_5+$ gasoline stream; and recycling a portion of the $C_5+$ gasoline stream from the debutanizer tower to the sorption fractionator as sorbent liquid.

11. The process of claim 1 wherein the heavy hydrocarbon liquid stream recovered from the primary stage effluent consists essentially of $C_5+$ hydrocarbons rich in $C_6$–$C_9+$ aromatics.

12. The process of claim 11 wherein the heavy hydrocarbon liquid stream is fractionated to recover $C_9+$ aromatics and a liquid sorbent stream.

* * * * *